United States Patent [19]

Wirtz-Peitz et al.

[11] 4,358,442

[45] Nov. 9, 1982

[54] ROSMARINIC ACID-PHOSPHOLIPIDE-COMPLEX

[75] Inventors: Ferdinand Wirtz-Peitz, Pulheim; Manfred Probst, Frechen; Johannes Winkelmann, Cologne, all of Fed. Rep. of Germany

[73] Assignee: Nattermann & Cie GmbH, Cologne, Fed. Rep. of Germany

[21] Appl. No.: 215,425

[22] Filed: Dec. 11, 1980

[30] Foreign Application Priority Data

Dec. 22, 1979 [DE] Fed. Rep. of Germany ....... 2952115

[51] Int. Cl.$^3$ .................... A01N 57/26; A61K 31/685
[52] U.S. Cl. ...................................... 424/199; 260/403
[58] Field of Search ........................ 260/403; 424/199

[56] References Cited

U.S. PATENT DOCUMENTS 4,271,196  6/1981  Schmidt .............................. 424/199

OTHER PUBLICATIONS

Chem. Absts., vol. 82, No. 167491r, "Phenolic Acid from Ragin", (1975).

Primary Examiner—John F. Niebling
Attorney, Agent, or Firm—Pearne, Gordon, Sessions, McCoy & Granger

[57] ABSTRACT

The present invention is directed to a new rosmarinic acid-phospholipide-complex product containing rosmarinic acid and the phospholipide in a molar ratio of 1:2. The invention is further directed to a process for producing the same and to pharmaceutical preparations containing the same.

7 Claims, No Drawings

ROSMARINIC ACID-PHOSPHOLIPIDE-COMPLEX

A large number of compounds are used already in the treatment of various inflammatory diseases. There are known for instance steroids, various pyrazolone derivatives, phenyl acetic acid derivatives or phenyl propionic acid derivatives, various indol acetic acid, in particular indometacin.

All anti-inflammatory agents used at present however have the disadvantage of showing substantial undesired side effects such as pyrosis, formation of ulcera and even gastro-intestinal hemorrhage.

It is an object of the present invention to find new products which are less toxic and have an improved compatibility to the stomach.

It has been surprisingly found that the new rosmarinic acid-phospholipide-complexes according to the present invention have an excellent anti-inflammatory effectiveness and a considerably increased therepeutic range of applicability in comparison to the compounds known in this field. The new complexes furthermore show anti-arteriosclerotic and immunostimulating properties. Furthermore, the new products show an extremely low toxicity and an excellent compatibility to the stomach. Rosmarinic acid, i.e. 3,4-dihydroxy-α-[[3-(3.4-dihydroxyphenyl)-1-oxo-2-propenyl]-oxy]-phenyl-propionic acid, is a compound occurring in various plants such as Rosmarinus officinalis (Ricerca sci. 1958, vol 28, p. 2329 to 2333), Melissa officinalis (Arch. Pharm. 1960, vol. 293, p. 1043 to 1048) or Teucrium scorodonia (Planta Med. 1965, vol. 13, 3, p. 331 to 345). Rosmarinic acid may be collected by extraction from such plants. Furthermore, rosmarinic acid may be recovered from plant cell cultures of Coleur blumei (Naturwissenschaften 1977, vol. 64, 11, p. 585 to 586).

Rosmarinic acid containing extracts have been tested for a circulation stimulating activity (Deutsche Apotherker-Zeitung 1964, vol. 104 p. 287 to 289) and for antimicrobial properties (N. Z. Alimkhodzhaeva et al., Chemical Abstracts, vol. 82, 167491). An antiphlogistic or anti-inflammatory activity up to now has not been published for rosmarinic acid. The new complexes of rosmarinic acid and phospholipides have not yet been described and are characterized by their excellent activity and very good compatibility.

Phospholipides which may be used in the preparation of the rosmarinic acid-phospholipide-complex products according to the present invention may be naturally occurring or synthetic phospholipides. Naturally occurring phospholipides (of plant or animal origin) are in particular phosphatidylcholine, phosphatidylethanolamine, phosphatidylinosite, phosphatidylserine, cephaline, lysolecithine, phosphatidylglycerol recovered for instance from soybeans or eggs, as well as mixtures from several such phospholipides. Such phospholipides are for instance phosphatidylcholine products of phosphatidylcholine mixtures known as trade products Phospholipon 100, Phospholipon 100 H or Phospholipon 80 and Phospholipon 45 as well as calcium phosphatidylcholine chlorine.

Phospholipon 100 is a 95% natural phosphatidylcholine recovered from soybeans,

Phospholipon 100 H is a 98% fully hydrogenated phosphatidylcholine from soybeans, Phospholipon 80 are phospholipides from soybeans containing 75% phosphatidylcholine and 12% phosphatidylethanolamine, Phospholipon 45 are alcoholic phospholipides from soybeans containing 55% phosphatidylcholine.

Synthetic phosphatides are for instance ditetradecanoylphosphatidylcholine, dihexadecanoylphosphatidylcholine, dioleylphosphatidylcholine or dilinolylphosphatidylcholine and in particular dipalmitoylphosphatidylcholine.

The best results are obtained with, and, therefor, most preferred are, phosphatidylcholine, hydrogenated phosphatidylcholine and calciumphosphatidylcholine chloride as it is described in German patent application P 29 51 681.2 filed Dec. 20, 1979.

For producing the new complex products according to the present invention, rosmarinic acid and the phospholipide are subjected to reaction in a molar ration of 1:2. The reaction is carried out with thorough emulgation and mixing in water.

The antiphlogistic activity is determined in the rat paw edema test according to Hillebrecht (see J. Hillebrecht, Arzneim, Forsch. 1954, vol. 4, p. 607). In this test there is produced an edema in one of the hindpaws of each rat weighing 200 to 250 grams by subplantaneous administration of Carragenin (0.5% in 0.9% NaCl solution) in an amount of 0.1 ml of the solution for each paw. After administration of the test compound which should be administered in an amount generally not increasing a volume of 10 cc. per each kg of body weight, the volume of the paw is determined by means of an overflowing water container. 3 hours after administration the final volume of the paw is determined. The test is carried out with 10 test animals and 10 control animals with identical sex per each dose and is repeated with the same number of test animals of the other sex. For evaluation there is determined the percent decrease of the edema in comparison to the control group.

The following test results were obtained:

TABLE 1

| | Antiphlogistic activity | | | | | |
| | Rosmarinic acid-phospholipide-complex | | | Indometacin | | |
| --- | --- | --- | --- | --- | --- | --- |
| dose (mg/kg p.o.) | 0,1 | 1,0 | 10,0 | 3,2 | 5,6 | 8,3 |
| % retardation of edema formation | −22 | −24 | −29 | −21 | −34 | −49 |

The ulcera formation is determined according to W. J. R. Whittle, Brit. J. Pharmacology 1975, vol. 55, p. 242 to 243, L. Mariani, Europ. J. Toxicol. Eviron, 1975, vol. 8, p. 335 to 339, R. Menguy and L. Desbaillets, Proc. Soc. Exp. Bio. vol. 125, p. 1108. In this test there are used 10 female and 10 male wistar rats (120 to 150 g) per each dose and each control test which rats were kept fasting for 16 hours. A bleeding stomach ulcus was provocated by oral application of the active compound to be tested. 3.5 hours after administration the test animals were killed, the stomach was taken out and opened along the large curvature and fixed to a Styropor plate. There is determined the mean factor of ulcus production for each test group and each control group.

TABLE 2

| Ulcus inducing activity in rats | | | | | | |
|---|---|---|---|---|---|---|
| | Rosmarinic acid-phospholipide-complex | | | Indometacin | | |
| dose (mkg/kg p.o.) | 10 | 100 | 316 | 3.2 | 5.6 | 7.5 |
| effectiveness | 0 | 0 | 0 | ++ | +++ | +++ |

0 = no ulcus formation
+ = moderate ulcus formation
++ = considerable ulcus formation
+++ = very high ulcus formation
The toxicity is determined in the mouse.

TABLE 3

| | Rosmarinic acid-phospholipide-complex | Indometacin |
|---|---|---|
| dose (mg/kg p.o.) | 1000 | 38 |
| death rate (4) | 0 | 50 |

As follows from the above tables, the new complex compounds according to the present invention produce an excellent antiphologistic activity, have a very low toxicity and cause no ulcus formation at all.

The rosmarinic acid-phospholipide-complex compounds according to the present invention may be easily converted to pharmaceutical preparations containing the same by mixing the active compound with usual inorganic or organic, solid or liquid, pharmaceutically useful carrier materials. Such pharmaceutical preparations may be administered enterally or parenterally.

Thus, there are used tablets or gelatine capsules which contain the active compound together with diluents such as lactose, dextrose, sucrose, mannitol, sorbitol, cellulose and/or glycerol and lubricants such as silica, talcum, stearic acid or salts thereof such as magnesium or calcium stearate, and/or polyethyleneglycol. Tablets may further contain adhesives such as magnesiumaluminiumsilicate, starch such as corn starch, wheat starch or rice starch, gelatine, methylcellulose, sodium carboxymethylcellulose and/or polyvinylpyrrolidone and, if desired, expander agents such as agar, alginic acid or a salt thereof such as sodium alginate, and/or effervescent preparations or adsorbing agents, colouring agents, flavouring agents or sweeteners. The rosmarinic acid-phospholipide-complex compounds may be also used as solutions which may be injected, for instance intravenously administered or administered as infusion. Such solutions preferably represent isotonic aqueous solutions or suspensions which may be produced for instance as lyophilisated products containing the active ingredient alone or together with suitable carriers, which are dissolved in the appropriate liquid before use. The pharmaceutical preparations may be produced in manners knows per se, for instance by usual mixing, granulating, pelleting, dissolution and/or lyophilisation.

The following examples serve to illustrate the present invention without however limiting the same thereto.

EXAMPLE 1

100 mg. of rosmarinic acid (molecular weight: 364) and 46.1 mg. of Phospholipone 100 H (molecular weight: 800) (molar ratio 1:2) are added to 100 ml. of water and dispersed by vivid stirring. After prolonged standing there is obtained a sediment which again is dispersed by a short shaking. There is obtained a solution of the rosmarinic acid-phospholipide-complex of the fully hydrogenated phosphatidylcholine.

EXAMPLE 2

10 mg. of rosmarinic acid are dissolved in 100 cc. of water. 47.5 mg. of fully hydrogenated calcium phosphatidylcholine chloride are added thereto and dispersed therein with vivid stirring. After standing for a prolonged period of time there is formed a sediment which again can be dispersed by short shaking.

The complex formation is determined by physico-chemical measurement in chloroform/methanol with dipalmitoylphosphatidylcholine marked with $^{31}P$. The results show that there is formed a hydrophilic complex between the phospholipide and rosmarinic acid. The time of relaxation for the phospholipide marked with $^{31}P$ in usual solutions and mixtures is 0.6 sec. and is decreased by complex binding to rosmarinic acid to 0.4 sec.

What we claim is:

1. Rosmarinic acid-phospholipide-complex.
2. Rosmarinic acid-phospholipide-complex according to claim 1 wherein 2 moles of phospholipide are present per each mole of rosmarinic acid.
3. Complex according to claim 1 characterized in that the phospholipide is a natural or synthetic phospholipide.
4. Complex according to claim 3 wherein the phospholipide is a natural or synthetic phosphatidylcholine.
5. Complex according to claim 4 characterized in that the phospholipide is phosphatidylcholine, hydrogenated phosphatidylcholine or calcium phosphatidylcholine chloride.
6. Process for the production of the rosmarinic acid--phospholipide-complex as claimed in claim 2 wherein rosmarinic acid is subjected to reaction with a phospholipide in a molar proportion of 1:2 with stirring.
7. A pharmaceutical preparation comprising a pharmaceutically effective amount of a rosmarinic acid-phospholipide-complex as claimed in claim 1.

* * * * *

UNITED STATES PATENT AND TRADEMARK OFFICE
CERTIFICATE OF CORRECTION

PATENT NO. : 4,358,442
DATED : November 9, 1982
INVENTOR(S) : Ferdinand Wirtz-Peitz et al.

It is certified that error appears in the above—identified patent and that said Letters Patent is hereby corrected as shown below:

Column 4, line 7, delete "100 mg." and substitute therefor
--10 mg.--.

Signed and Sealed this

Nineteenth Day of April 1983

[SEAL]

Attest:

GERALD J. MOSSINGHOFF

Attesting Officer     Commissioner of Patents and Trademarks